United States Patent
Purow et al.

(10) Patent No.: US 7,244,245 B2
(45) Date of Patent: Jul. 17, 2007

(54) SHEATH DEVICE WITH DRESSING FOR PREVENTION OF PNEUMOTHORAX.

(75) Inventors: Benjamin Warren Purow, Takoma Park, MD (US); Michael P. Chu, Chicago, IL (US)

(73) Assignee: Benjamin Purow, Charlottesville, VA (US)

( * ) Notice: Subject to any disclaimer, the term of this patent is extended or adjusted under 35 U.S.C. 154(b) by 675 days.

(21) Appl. No.: 10/390,457

(22) Filed: Mar. 17, 2003

(65) Prior Publication Data
US 2003/0233073 A1    Dec. 18, 2003

Related U.S. Application Data

(63) Continuation of application No. 09/689,545, filed on Oct. 12, 2000, now Pat. No. 6,569,121.

(51) Int. Cl.
*A61M 5/32* (2006.01)
(52) U.S. Cl. ........................... 604/180; 128/898
(58) Field of Classification Search ........... 604/174, 604/175, 180, 246, 247, 263, 264, 163, 164.08, 604/304, 305, 307, 523, 93.01; 128/898, 128/849, 850, 852, 856
See application file for complete search history.

(56) References Cited

U.S. PATENT DOCUMENTS

| | | | |
|---|---|---|---|
| 3,253,594 A * | 5/1966 | Matthews et al. ..... | 604/103.03 |
| 3,487,837 A | 1/1970 | Petersen ...................... | 128/349 |
| 3,777,757 A | 12/1973 | Gray et al. .................. | 128/276 |
| 4,392,853 A | 7/1983 | Muto .......................... | 604/171 |
| 4,596,554 A | 6/1986 | Dastgeer ...................... | 604/54 |
| 4,632,671 A | 12/1986 | Dalton ........................ | 604/174 |
| 4,681,564 A | 7/1987 | Landreneau ................. | 604/97 |
| 4,767,411 A | 8/1988 | Edmunds .................... | 604/180 |
| 4,813,941 A | 3/1989 | Shea ........................... | 604/247 |
| 4,943,284 A | 7/1990 | Erlich ......................... | 604/263 |
| 5,419,776 A | 5/1995 | Baer ........................... | 604/246 |
| 5,478,333 A * | 12/1995 | Asherman, Jr. ............ | 604/304 |
| 5,662,616 A | 9/1997 | Bousquet .................... | 604/175 |
| 5,738,661 A | 4/1998 | Larice ......................... | 604/180 |
| 5,807,341 A | 9/1998 | Heim .......................... | 604/174 |

* cited by examiner

*Primary Examiner*—Nicholas Lucchesi
*Assistant Examiner*—Theodore J. Stigell
(74) *Attorney, Agent, or Firm*—Brinks Hofer Gilson & Lione

(57) ABSTRACT

A sheath device comprises a substantially rigid elongated body adapted to receive a chest tube. The body includes a first end and a second end, flexible seal at the first end, and an air-impermeable flexible joint at the second end. A base having a first side and a second side is provided at the joint, wherein the first side is connected with the flexible joint and the second side includes an adhesive for securing the base to a patient's chest. A method of preventing pneumothorax in a patient having a chest tube removed comprises attaching the sheath device to the patient's chest at the time of the chest tube placement, later withdrawing the chest tube into the airtight chamber of the sheath, and sealing the sheath device. Removing the base and flexible joint of the sheath device from the body of the sheath device leaves an air-impermeable dressing on the patient's chest.

20 Claims, 7 Drawing Sheets

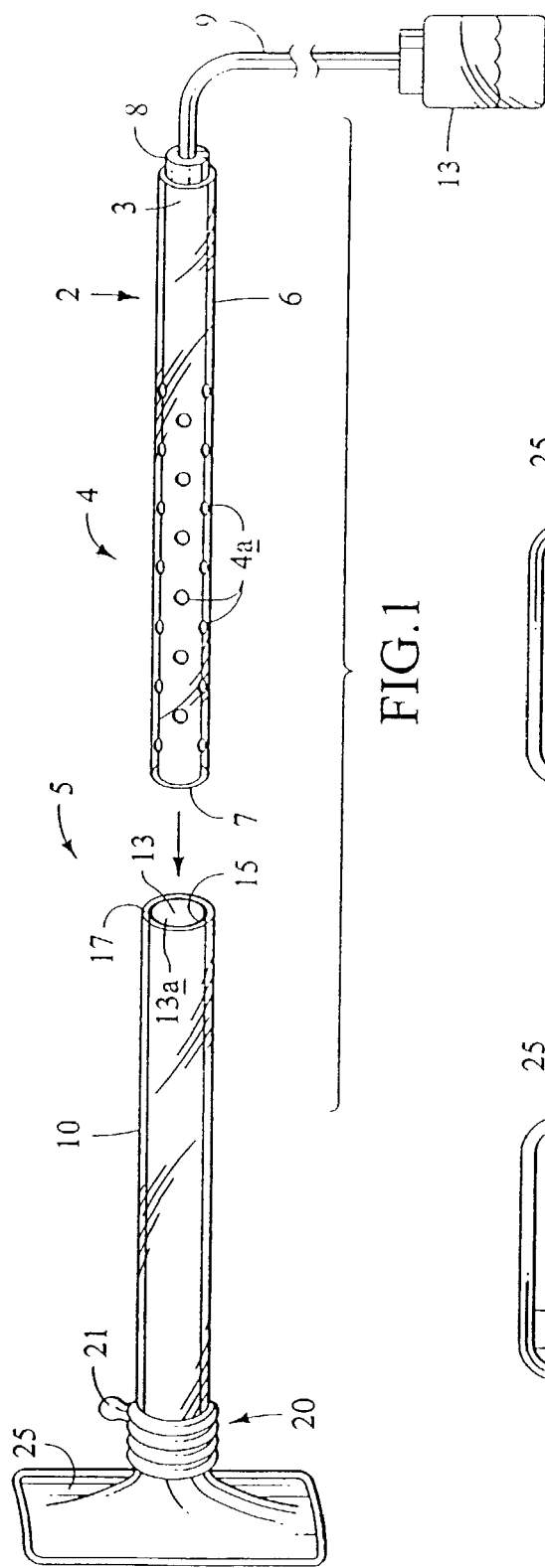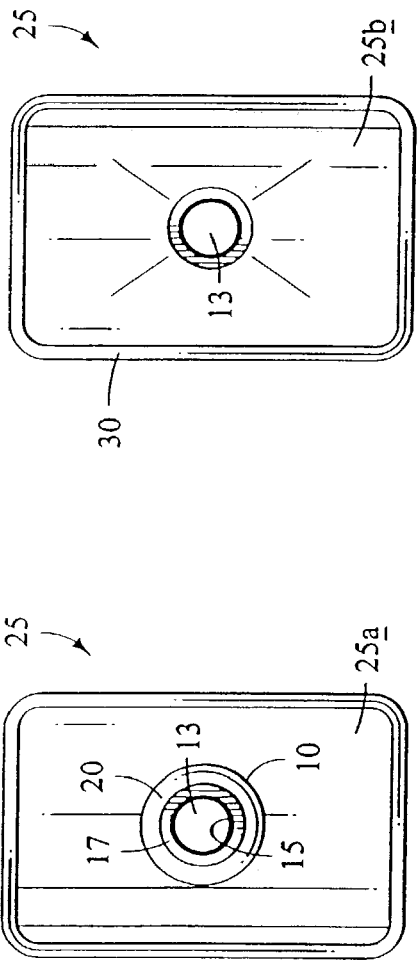

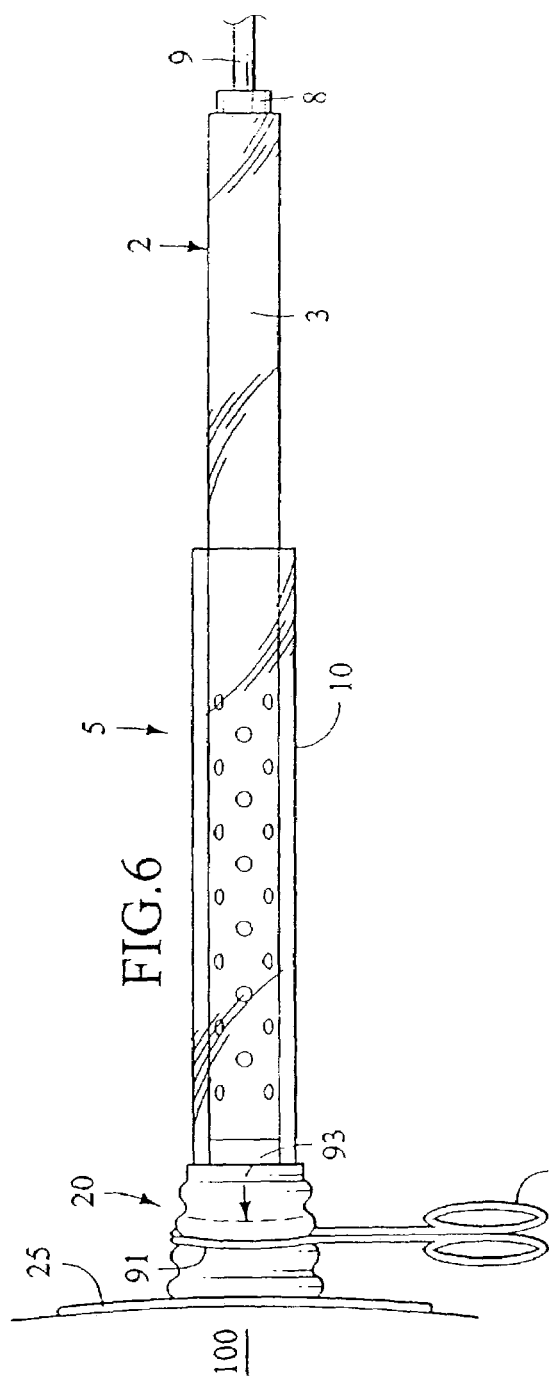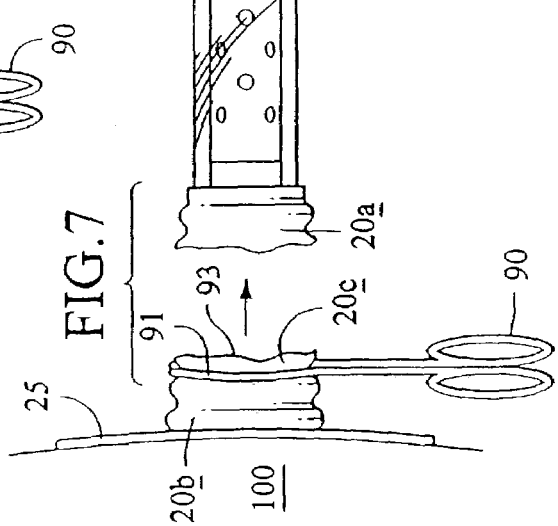

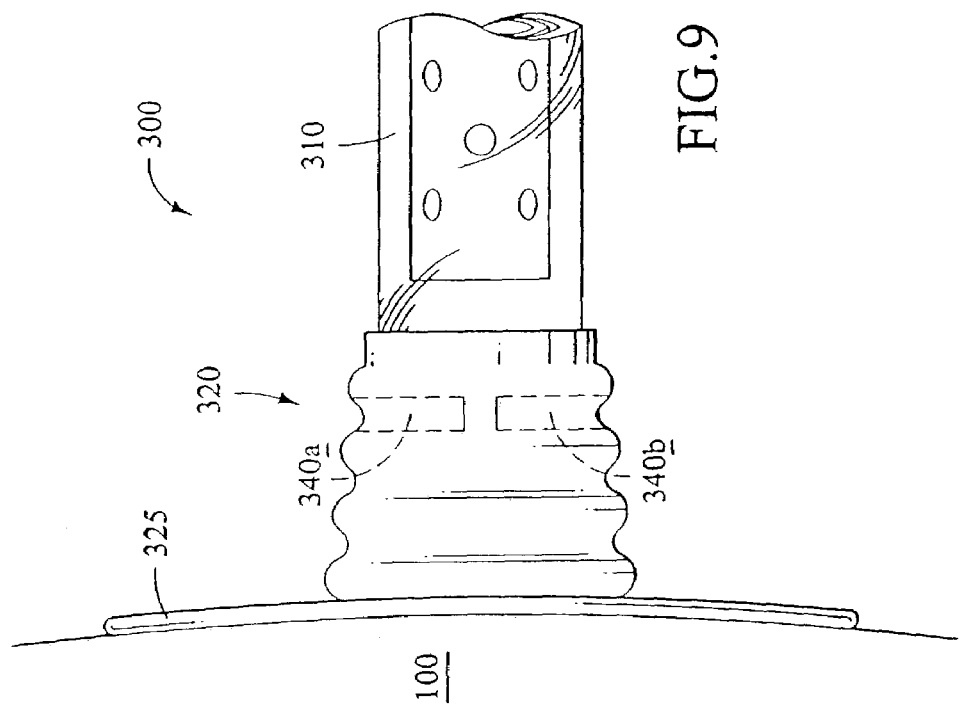
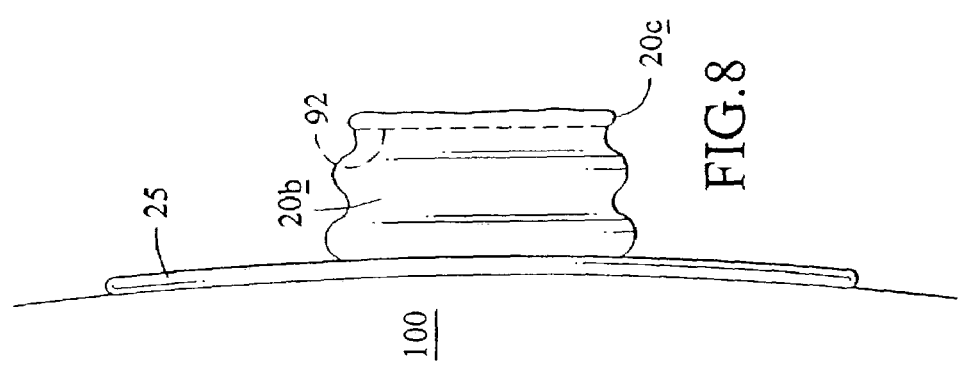

SHEATH DEVICE WITH DRESSING FOR PREVENTION OF PNEUMOTHORAX.

This application is a continuation of application Ser. No. 09/689,545, filed Oct. 12, 2000, now U.S. Pat. No. 6,569,121.

BACKGROUND OF THE INVENTION

In a healthy person, the pleural chest cavity is generally an airtight, airless environment. During normal respiration, the contraction of the diaphragm increases the volume of the cavity, which in turn decreases the pressure therein and causes the lungs to expand. Normally, air cannot enter or escape the pleural cavity.

Patients who have fluid or air in this cavity may be treated by inserting a chest tube into the pleural cavity to drain this fluid or air. The chest tube typically comprises a plastic tube having drainage holes at its tip and in a section of its sidewall and is inserted through an incision in the wall of the patient's chest. Ordinarily, the tube is connected to a collection container for holding the drained fluids. When the cavity of a given patient has been drained and the underlying cause of the fluid buildup has been addressed, the chest tube must be removed from the patient. This is done conventionally by withdrawing the tube and suturing the incision closed. In some patients, most notably children, no suturing is done, and petroleum jelly is used to seal the opening around the chest tube during the withdrawal of the tube. A gauze dressing is then placed over the incision and secured to the skin. However, if an inspiration occurs while the tube is partially pulled or before the incision is sealed, air can enter the pleural cavity due to the negative pressure therein.

Pneumothorax, or the passage of air into the pleural cavity, is undesirable because it allows the chest cavity to lose pressurization and decreases the expansion capability of the lungs. Complications of pneumothorax can include the collapse of part or all of a lung caused by pressure from free air in the chest cavity between the two layers of the pleura, which are thin membranes that cover the lung. Further complications associated with pneumothorax include respiratory failure and lung infection. Hospitalization and treatment with special equipment following minor surgery may be necessary for patients who suffer from pneumothorax.

Pneumothorax risk while removing a chest tube from a patient may be minimized by limiting the amount of air that can enter the chest cavity during and after removal of the tube. Ordinarily, upon removal of the chest tube from the body, a doctor or technician will attempt to hold the opening into the chest closed with the hand while undertaking to suture or bandage the opening. In many cases, however, the dressing placed over the opening is not completely air impermeable, or the attendant may have difficulty holding the opening closed while suturing the opening. While the pressure leaks may be minimal, these procedures are cumbersome to undertake, and the relatively minor leaks may compromise pressurization within the chest cavity and cause the patient some distress while breathing. More seriously, dressings or sutures may become completely undone, thereby allowing the cavity to depressurize more rapidly. This would, of course, more severely affect the ability of the patient to respirate properly and complicate a pneumothorax condition.

SUMMARY OF THE INVENTION

In accordance with the present invention, a combination sheath and dressing device is provided for use in assisting in the removal of chest tubes from patients and the dressing of the tube incision in the chest. The device allows a chest tube to be removed without allowing air into in the chest cavity during the removal process, and facilitates the healing of the chest incision after the tube is removed. The device preferably includes an air-impermeable base dressing which is placed over the opening into the chest cavity. The base is connected to a tubular housing for receiving a conventional chest tube. The housing, which is attached to the dressing via a flexible boot structure, is used to allow some movement of the chest tube within the housing while maintaining pressure in the chest cavity. The flexible boot allows the dressing to be closed without compromising the pleural airspace.

In one aspect of the invention, a sheath device comprises a substantially rigid elongated body adapted to receive a chest tube. The body includes a first end and a second end, flexible seal at the first end, and an air-impermeable flexible joint at the second end. A base having a first side and a second side is provided at the joint, wherein the first side is connected with the flexible joint and the second side includes an adhesive for securing the base to a patient's chest. The base provides an air-impermeable connection between the flexible joint and a patient's chest cavity.

In another aspect of the invention, a method of preventing pneumothorax in a patient having a chest tube removed is provided. The method includes the steps of attaching to the patient's chest an air-impermeable sheath device having a body, a joint, and a base such that the flexible joint and the base are removable from the body, and removing the chest tube through the sheath device. After the chest tube is pulled out of the patient's chest and before the chest tube is entirely removed from the sheath device, a portion of the device is sealed and separated, thereby leaving an air-impermeable dressing over the patient's chest.

In still another aspect of the invention, a sheath device for use on a patient having a chest tube inserted into the patient's chest cavity includes a substantially rigid, hollow, air-impermeable body configured to fit snugly around a chest tube. The body includes a first end and a second end, seal at the first end of the body, an air-impermeable flexible sealable joint at the second end of the body, and a base. The base includes a first side and a second side, and the first side is connected with the flexible joint. The second side includes an adhesive for securing the base to the patient's chest, and the base provides an air-impermeable connection between the flexible joint and the patient's chest cavity. The flexible joint and base together may form an air-impermeable dressing on the patient's chest.

The present invention provides the foregoing and other features, and the advantages of the invention will become further apparent from the following detailed description of the presently preferred embodiments, read in conjunction with the accompanying drawings. The detailed description and drawings are merely illustrative of the invention and do not limit the scope of the invention, which is defined by the appended claims and equivalents thereof.

BRIEF DESCRIPTION OF SEVERAL VIEWS OF THE DRAWINGS

Note that for purposes of clarity, the drawings herein are not drawn to scale.

FIG. 1 is a perspective view of the sheath device of the present invention along with a chest tube for use therewith;

FIG. 1A is a view of the sheath device shown in FIG. 1 with the chest tube removed;

FIG. 1B is a rear view of the sheath device shown in FIG. 1A;

FIG. 6 is a side view showing the sheath device of the present invention being temporarily sealed with a clamp;

FIG. 7 is a side view similar to that of FIG. 6 showing the clamped section of the sheath device being separated from the body portion of the sheath device and the chest tube;

FIG. 8 shows the sealed joint and dressing portion of the sheath device attached to the patient and configured as a wound dressing;

FIG. 9 is a side view of a second embodiment of the sheath device of the present invention showing an adhesive area within the joint portion of the device.

DETAILED DESCRIPTION

Figure 2:
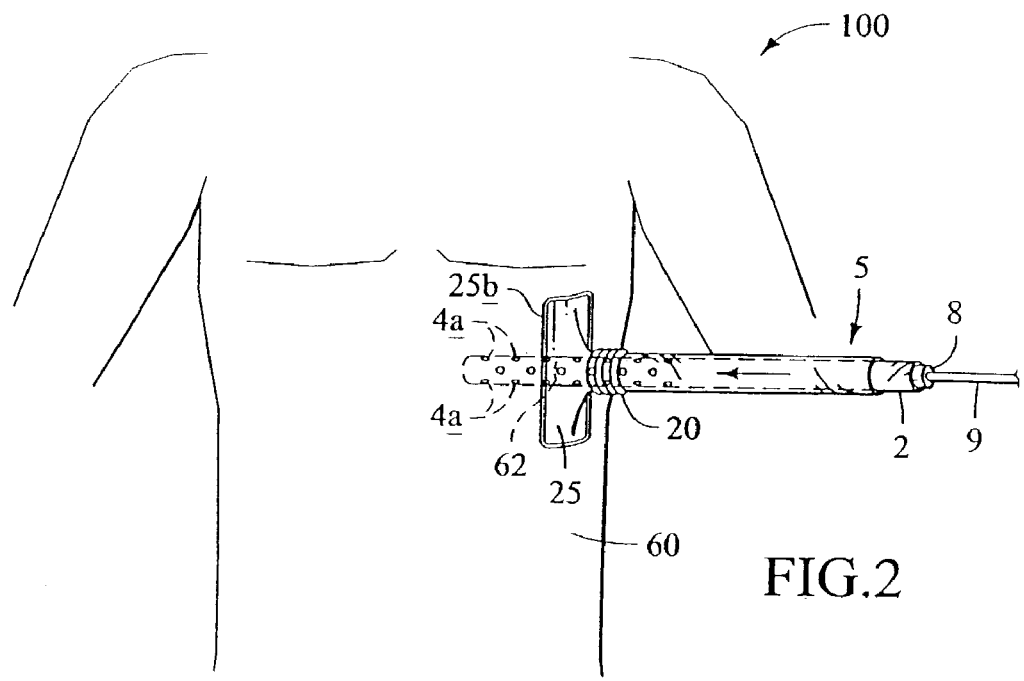
FIG. 2 is a perspective view of the sheath device of the present invention installed on the chest wall of a patient, and including a chest tube inserted therein.

Referring to FIG. 1, a sheath device 5 is shown with a conventional chest tube 2 for placement therein. The sheath device 5 has a body 10, a seal 15, a joint 20 and a base 25. Preferably, the body 10 is substantially rigid. By "substantially rigid", it is meant that the body 10 does not collapse onto itself when air passes through it at the pressures commonly associated with the thoracic cavity. The body 10 is preferably formed from an air-impermeable material. By "air-impermeable", it is meant that air cannot pass through the material, or, that if it can, it passes through so slowly and at such a minimal volume that it does not interfere with the purpose of the present invention. While it is preferred that the body 10 is substantially rigid, a portion of the body 10 may comprise a flexible portion so that a portion of the chest tube 2 may be gripped by the user while still within the body 10.

Preferably, the body 10 is made of a clear or generally opaque medical-grade, sterile plastic. For reasons that will become clear below, it is also preferable that the distal end 7 of the chest tube be at least partially visible through the wall of the body 10. The body 10 is elongated in a tubular shape, and adapted to fit around the chest tube 2. Any dimensions are acceptable, so long as they do not interfere with the ability of the body 10 to fit around the chest tube 2 and for the chest tube 2 to be slidably retained therein. The interior of the body 10, along with the base 25 and the joint 20, preferably enclose an interior, continuous airspace.

The seal 15 is preferably a substantially air-impermeable, elastomeric O-ring. A small quantity of sterile lubricant may be used to facilitate slidable movement of the chest tubes through the seal and within the body 10. Preferably, the interior diameter of the O-ring will deform slightly to allow the chest tube 2 to slidably pass within the opening of the seal 15. The seal 15 is preferably mounted to the interior of the body 10 adjacent the distal end 17 of the body 10. The interior portion of the seal 15 preferably extends past the sidewalls of the body 10 and partially into the interior 13 of the body 10. This ensures that air cannot escape at the interface between the distal end 17 and the outer wall 3 of the chest tube 2 when it is received within the body 10. Note that the seal 15 may be located within the body 10 in a position other than near the distal end 17. For example, it may be located within the body 10 towards the middle of the body 10 to allow a greater slidable area for the chest tube and relative to the body 10.

The chest tube 2 preferably comprises a forward portion 4 that defines a plurality of drainage holes 4a around the sidewall 3 of the tube 2. The drainage holes 4a assist in the collection of fluid from the thoracic cavity area and allow the fluid to drain towards a rearward portion 6 of the tube 2. A coupling 8 is preferably provided on the distal end of the rearward portion 6 to connect the chest tube 2 to a drainage tube 9. The drainage tube 9 is in turn preferably connected to a collection container 13 for holding the collected chest fluid.

The joint 20 is preferably a flexible and air-impermeable boot that joins the body 10 with the base 25. By "flexible" it is meant that the material forming the joint 20 can be bent with minimal effort. The joint includes ridged annular raised portions 21 along its walls to provide a corrugated structure that allows the joints to be bent to approximately 90° without closing off its internal throughgoing airspace. The joint 20 is attached at one end with the base 25 and attached at the opposing end with the body 10. Preferably, the joint 20 is constructed of a latex material having a wall thickness sufficient to support its annular corrugated structure. Other, non-corrugated configurations may of course be utilized to lend flexibility to the structure of the joint 20. In a first embodiment, the joint 20 between body 10 and the chest tube 2 may be manually sealable, as described below.

As shown in FIG. 1a, the base 25 includes a front side 25a that is sealed to the joint 20. The base 25 is preferably molded using a planar, substantially rigid plastic material having a slightly convex curve toward the mounted joint 20. As shown in FIG. 1b, the base 25 preferably defines a second, slightly concave side 25b that carries an attachment mechanism for attaching the sheath 5 to a patient. Preferably, the attachment mechanism is a medically acceptable adhesive deposited along a rim 30 of the base 25. The adhesive allows an airtight seal between the sheath 5 and the skin of the chest wall. The attachment mechanism can also include staples, stitches, and any other sealable, substantially air-impermeable attachment mechanism known in the art.

FIG. 2 shows the sheath device 5 mounted to the chest wall 60 of the patient 100. As shown in the drawing, the base 25, in particular, is mounted via an adhesive on the underside 25b of the base 25 to the skin of the patient 100 along the chest wall 60. Underneath the plastic film of the base 25, the incision opening 62 into the thoracic cavity or pleural airspace of the patient 100 is visible. The incision 62 allows the chest tube 2 to penetrate into the chest cavity of the patient. Typically, the forward portion of the chest tube containing the plurality of drainage openings 4a is inserted into the interior of the chest cavity 60 to collect fluids within the cavity. In such cases, the chest tube is usually inserted so that the forward portion is completely enclosed within the patient, and no openings are exposed on the outside of the chest incision 62. In most applications herein, the sterilized sheath device 5 is placed onto the chest wall 60 of the patient 100 at the time the chest tube 2 is inserted into the incision opening 62. This is preferred because the chest tube 2, the sheath body 10, the underside of the base 25, and the field around the incision opening 62 are sterile only at that time.

Figure 3:
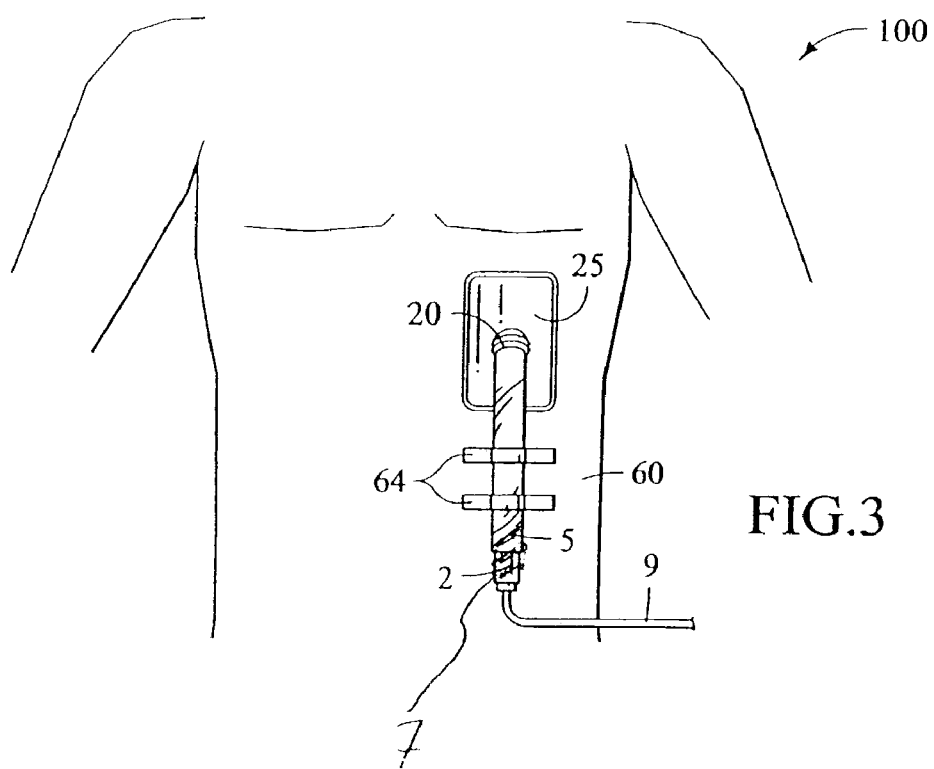
FIG. 3 is a perspective view of the sheath device as shown in FIG. 2 in a retained position against the patient's chest.

With the chest tube 2 positioned properly within the chest cavity, the sheath device 5 may be bent flush with the patient's chest 60 as shown in FIG. 3. Strips of adhesive tape 64 may be used to adhere the sheath 5 to the patient 100 while allowing the chest cavity to drain through the tubes. In this position, the chest tube 2 is partially protected within the body 10 and secured against the chest 60 by the tape 64 and the adhesive underneath the base 25. With the sheath device 5 and chest tube 2 in this secured position, the intubated patient has a reduced risk of the chest tube being accidentally pulled out of the chest.

As shown in FIG. 3, it is preferable to prevent movement of the chest tube 2 relative to the sheath device 5 by wrapping a piece of adhesive tape 7 around the distal end of the body 10 and a rearward portion of the chest tube 2 as shown. The tape 7 may also be wrapped around the interface between the chest tube 2 and the distal end of the body 10 to seal the interface and to further prevent compromise of the airspace within the sheath device 5. By securing the sheath device 5 and the chest tube 2 in the position shown in FIG. 3 and as described herein, a significant advantage of the invention becomes apparent, in that it becomes unnecessary to secure the chest tube 2 directly to the patient 100 using several large sutures. Such suturing to the skin of the patient 100 is common practice using the prior art.

Figure 4:
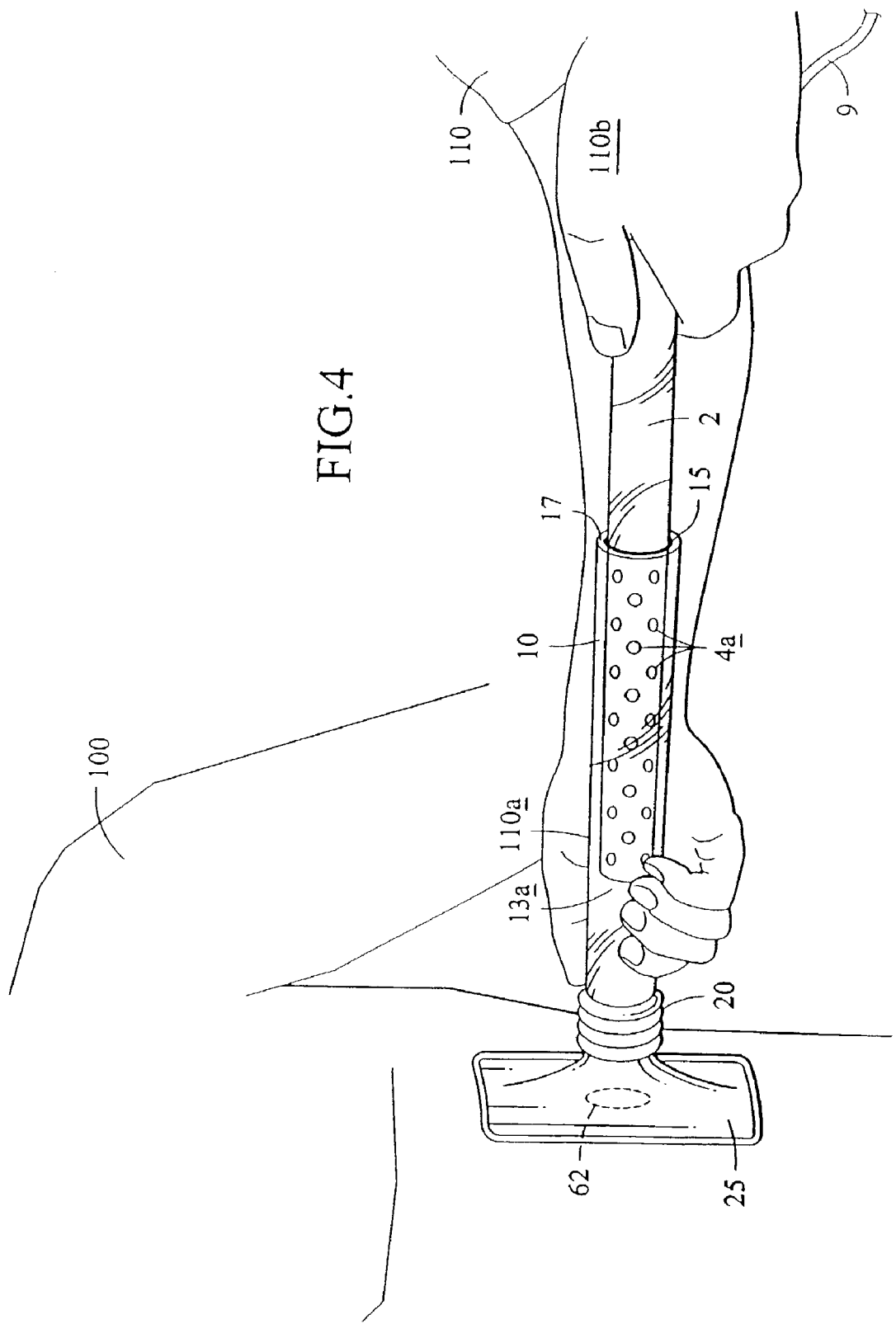
FIG. 4 is a perspective view showing the chest tube being removed manually from the sheath device of the present invention.

Using the present embodiment of the invention, a chest tube 2 may be removed from the patient's chest cavity without compromising the vacuum of the pleural airspace. The undertaking of the removal procedure is shown in the perspective drawing of FIG. 4. As shown in the Figure, a medical technician 110 preferably removes the chest tube 2 from the patient 100 by grasping the sheath body 10 using a hand 110a and the chest tube using a hand 110b. During the removal procedure, the technician 110 preferably holds the body 10 stationary relative to the patient so that undue pressure is not exerted against the base 25 to compromise the adhesive relationship between the base 25 and the patient 100. At the same time, the technician 110, using the hand 110b, withdraws the chest tube 2 from the patient 100 by pulling the tube 2 outwardly from the incision 62 and relatively out through the distal end of the body 10 of the sheath device 5. The O-ring seal 15 maintains the vacuum pressure within the chest cavity of the patient 100 by maintaining the pressure within the airspace 13a within the body 10.

Figure 5:
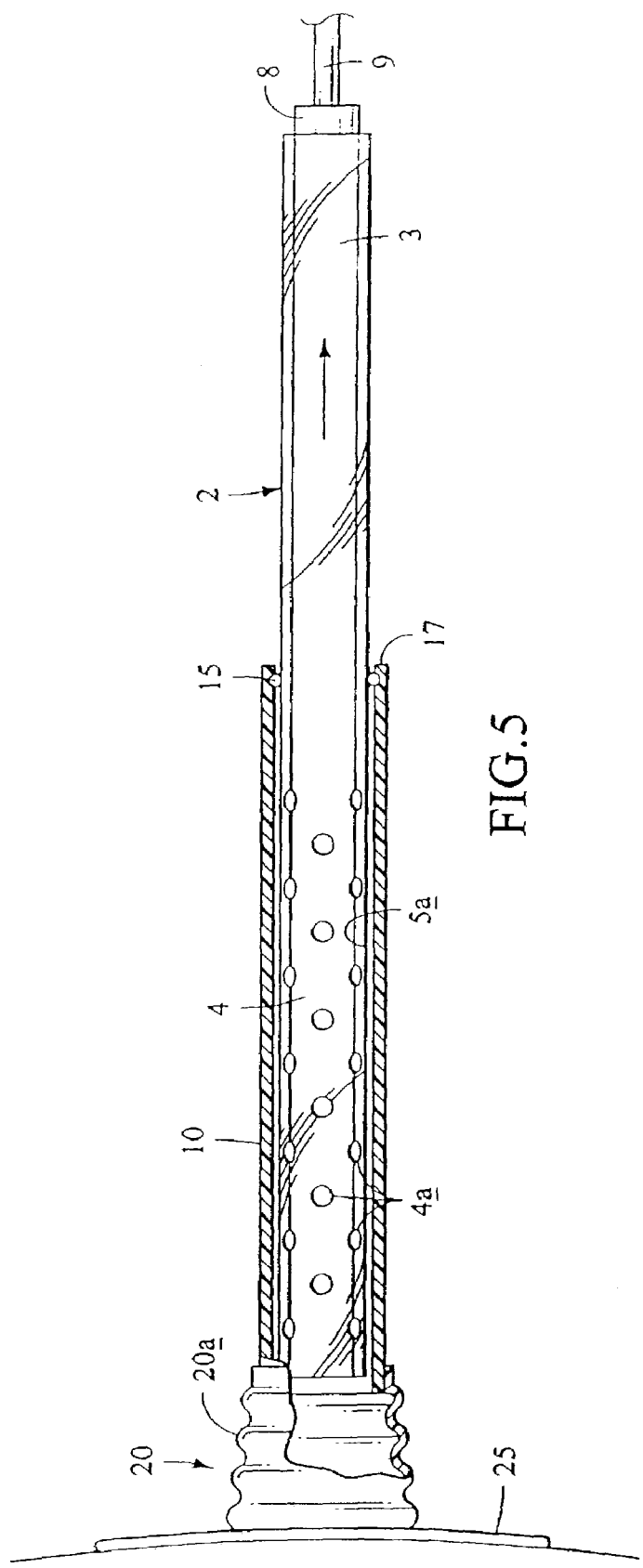
FIG. 5 is a cut-away side view of the sheath device of FIG. 1 showing the chest tube removed from the cavity of the patient but retained within the sheath device of the present invention.

The chest tube 2 is fully withdrawn from the patient 100 when the distal end of the tube 7 is completely removed from the incision 62 as shown in the side view of FIG. 5. It is important that the forward portion 4 of the chest tube 2 not be withdrawn past the seal 15. If any of the openings 4a have passed the seal 15 (in this embodiment just past adjacent the distal end 17 of the sheath body 5) the continuous airspace within the chest tube 2 and the patient's pleural cavity will be compromised to atmospheric pressure outside of the patient.

Once the chest tube 2 is sufficiently withdrawn from the patient 100, the flexible joint 20 may be temporarily sealed off by a surgical hand clamp 90 as shown in FIG. 6. The hand clamp 90 preferably includes relatively flat clamping jaws 91 that pinch the walls of the flexible joint 20 together to prevent air from escaping from the pleural cavity. Once the flexible joint 20 is so sealed, the remaining portion of the sheath device 5 may be separated from the clamped portion of the flexible seal 20. This may be accomplished by using a knife or scissors to cut the flexible seal 20 along the line 93 as shown in FIG. 6. In the alternative, the flexible joint 20 may be pre-perforated or include a self-separating tab pull along the approximate area of the severing line 93 to simplify separation of the sheath device 5 from the clamped area.

Once the severing line 93 has been cut or otherwise separated, the flexible joint 20 will comprise two sections 20b and 20a. The remaining portion 20a including a portion of the flexible joint 20, the sheath body 10, and the chest tube 2 and its related components as separated from the clamped portion 20b may be discarded as shown in FIG. 7. The airspace within the pleural cavity and within the portion 20b of the flexible joint remains sealed by the clamp jaws 91, which leaves the medical technician's hands free to more permanently seal the portion 20b of the flexible seal. Preferably, the technician can sterilize the outer portion of the flexible seal 20 and run a surgical stitch or use adhesive to close the severed portion 20c to the right of the clamp jaw 91. In the alternative, the technician may use adhesive, tape, a heat-sealing apparatus or other known method to provide an airtight seal adjacent to the edge portion 93 of the severed portion 20c.

After the edge 93 is sealed, the clamp 90 may be removed, thereby leaving the sealed portions 20b and 20c of the flexible joint intact on the base 25, which in turn remains attached to the patient 100. The incision (not shown) will remain surrounded by the sterile environments of the base 25 and the flexible seal 20b for healing. In this configuration, the base 25 and remaining portions of the flexible seal 20b and 20c together comprise a sterile dressing over the incision. This remaining configuration is shown in FIG. 8. Advantageously, the chest tube 2 has been removed in an airtight and sterile environment, reducing the risk of pneumothorax and infection.

In another embodiment 300, the joint 320 may be automatically self-sealable, as depicted in FIG. 9. As shown in the Figure, the interior of the joint 320 includes self-sealing adhesive strips having portions 340a and 340b. Preferably, the adhesive portions of the strips 340a and 340b generally face each other. After the chest tube is removed past the joint 320 into the body 310, the adhesive strips 340a may be pinched manually onto adhesive strip 340b within the joint 320 from the outside of the joint 320, creating an air-impermeable seal in the joint 320. The body 310 and a portion of the joint 320 may then be separated from the sealed dressing portion as described above. As in the above-described embodiment, the automatically sealable embodiment provides a mechanism with which a chest tube is removed in an airtight environment, thereby significantly reducing the risk of pneumothorax.

Figure 10:
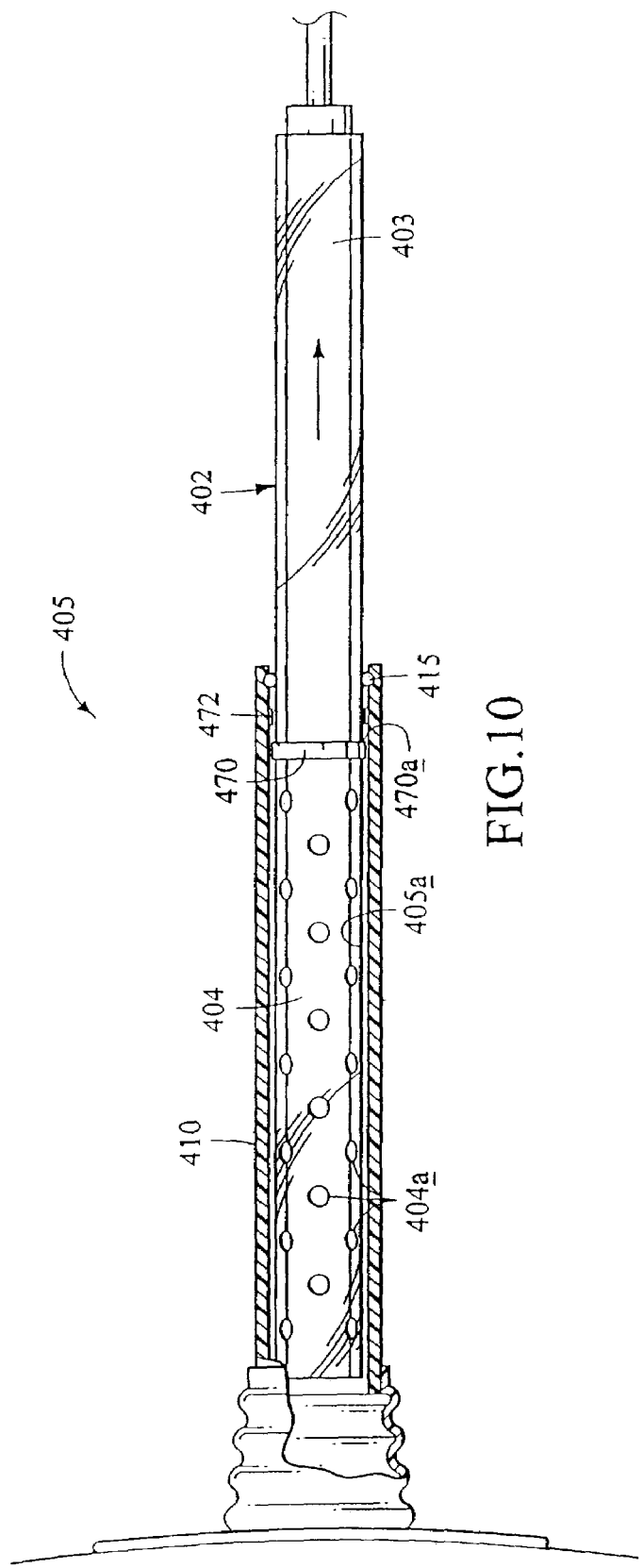
FIG. 10 is a side view of a third embodiment of the invention showing a stop means integrated therein.

In another embodiment of the invention, to further speed chest tube removal while preventing the accidental compromise of pleural pressure during the procedure, a stop means is provided on either the chest tube and/or the body of the sheath device to prevent the tube from being pulled too far out of the sheath device. This alternate embodiment is shown in FIG. 10. In this embodiment, the sheath device 410 is shown in a side cutaway view having a chest tube 402 inserted therein. The stop means is structured as a raised annular ring 470 joined substantially around the circumference of a portion of the rear portion 403 of the tube 402. Stop faces 472 are fixed to the inner wall 405a of the sheath body 405, and extend toward the internal axial airspace of the body 405. In the present embodiment, the stop faces 472 may comprise an annular ring positioned on the inner wall 405a or upstanding faces of other shapes. The faces 472 contact the rear face 470a of the annular ring 470 as the tube 402 is pulled outwardly from the sheath body 410, and thereby prevent the chest tube 402 from being pulled past the contact point between the face 470a and the faces 472. This prevents the forward portion 404 of the chest tube 402 from being pulled past the O-ring seal 415 and thereby compromising the airspace in the pleural cavity to atmospheric pressure. With the chest tube and sheath device in this configuration, both of these main components may be packaged and provided to medical personnel connected together in this fashion.

It should be appreciated that the present invention is capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is therefore indicated by the appended claims rather than by the foregoing description. All changes that come within the meaning and range of equivalency of the claims are embraced to be within their scope.

The invention claimed is:

1. A dressing device comprising:
    a substantially rigid, elongated body adapted to receive a chest tube, the body having a first end and a second end;
    a seal positionable between the body and the chest tube;
    an air-impermeable flexible joint at the second end of the body, the joint having a first portion, a second portion and an internal airspace therethrough; and
    a base having a first side and a second side, wherein the first side of the base is connected with the first portion of the flexible joint, and wherein the second side of the base includes an adhesive for securing the base to a patient's chest, the base providing an air-impermeable connection between the flexible joint and the patient's chest cavity;
    wherein the joint is sealable between the first portion and the second portion to close the airspace therethough.

2. The dressing device of claim 1 wherein the flexible joint may be bent.

3. The dressing device of claim 1 wherein the seal is an o-ring.

4. The dressing device of claim 1 wherein the flexible joint and base are together removable from the body.

5. The dressing device of claim 4 wherein at least a portion of the flexible joint and base are together removable from the body when a chest tube has traveled a predetermined distance through the dressing device.

6. The dressing device of claim 4 wherein the flexible joint and base are together manually removable from the body.

7. The dressing device of claim 1 wherein the flexible joint is automatically sealable, between the first portion and the second portion of the flexible joint, when a chest tube has been withdrawn from a patient's chest and the chest tube travels a certain distance into the body of the dressing device.

8. The dressing device of claim 1 wherein the flexible joint is manually sealable, between the first portion and the second portion of the flexible joint, when a chest tube has been withdrawn from a patient's chest and the chest tube travels a certain distance into the body of the dressing device.

9. The device of claim 1 wherein the seal is at the first end of the body.

10. A method of preventing pneumothorax in a patient having a chest tube inserted in the patient's chest, the method comprising:
    attaching to the patient's chest an air-impermeable sheath device having a body adapted to receive said chest tube, a flexible joint having a first portion and a second portion, and a base such that the flexible joint and base are removable from the body, said base, joint and body defining a sealed airspace, wherein said chest tube is positioned at least partially within said airspace;
    removing the chest tube from the patient's chest and receiving the tube into the body of the sheath device;
    sealing the sheath device after the chest tube is removed from the patient's chest and before the chest tube is entirely removed from the sheath device; and
    removing the chest tube from the sheath device, leaving an air-impermeable dressing over the patient's chest.

11. The method of claim 10 wherein the joint and the body are together removable from the base of the sheath.

12. The method of claim 10 wherein the sheath device is sealed automatically.

13. The method of claim 10 wherein the sheath device is sealed manually.

14. The method of claim 10 wherein the joint is sealable by adhesive pre-applied to the interior of the joint when a chest tube travels a certain distance into the body of the sheath.

15. A sheath device for use on a patient having a chest tube inserted into the patient's chest cavity, the sheath device comprising:
    a substantially rigid, hollow, air impermeable body configured to fit snugly around a chest tube, the body having a first end and a second end;
    an air-impermeable flexible expandable seal at the first end of the body;
    an air-impermeable flexible sealable joint, the joint having a first portion and a second portion, at the second end of the body; and
    a base having a first side and a second side, wherein the first side of the base is connected with the first portion of the flexible joint and wherein the second side of the base includes an adhesive for securing the base to the patient's chest; the base providing an air-impermeable connection between the flexible joint and the patient's chest;
    wherein the first portion of the flexible joint and the base are removable from the body and the second portion of the flexible joint such that when the first portion of the flexible joint and the base are together removed from the body and the second portion of the flexible joint, the first portion of the flexible joint and the base together form an air-impermeable dressing on the patient's chest.

16. The sheath device of claim 15 wherein the flexible joint is automatically sealable, between the first portion of the flexible joint and the second portion of the flexible joint, when the chest tube has been withdrawn from the patient's chest and the chest tube travels a certain distance into the body of the sheath.

17. The sheath device of claim 15 wherein the flexible joint is manually sealable between the first portion of the flexible joint and the second portion of the flexible joint.

18. The sheath device of claim 15 wherein the first portion of the flexible joint and the base are automatically removable from the body and the second portion of the flexible joint when a chest tube has been withdrawn from a patient's chest and the chest tube travels a certain distance into the body of the sheath.

19. A method of preventing pneumothorax in a patient having a chest tube inserted in the patient's chest, the method comprising:

attaching to the patient's chest an air-impermeable sheath device having a body adapted to receive said chest tube, a flexible joint having a first portion and a second portion, and a base such that the flexible joint and base are removable from the body, said base, joint and body defining a sealed airspace, wherein said chest tube is positioned at least partially within said airspace;

removing the chest tube from the patient's chest and receiving the tube into the body of the sheath device; and automatically sealing the sheath device leaving an air-impermeable dressing over the patient's chest after the chest tube is removed from the patient's chest and before the chest tube is entirely removed from the sheath device; and removing the second portion of the joint and the body from the first portion of the joint and the base, leaving the first portion of the joint and the base on the patient's chest as an air-impermeable dressing.

20. A method of preventing pneumothorax in a patient having a chest tube inserted in the patient's chest, the method comprising:

attaching to the patient's chest an air-impermeable sheath device having a body adapted to receive said chest tube, a flexible joint having a first portion and a second portion, and a base such that the flexible joint and base are removable from the body, said base, joint and body defining a sealed airspace, wherein said chest tube is positioned at least partially within said airspace;

removing the chest tube from the patient's chest and receiving the tube into the body of the sheath device; and manually sealing the sheath device leaving an air-impermeable dressing over the patient's chest after the chest tube is removed from the patient's chest and before the chest tube is entirely removed from the sheath device; and removing the second portion of the joint and the body from the first portion of the joint and the base, leaving the first portion of the joint and the base on the patient's chest as an air-impermeable dressing.

* * * * *